United States Patent
Timms

(10) Patent No.: US 9,655,765 B2
(45) Date of Patent: May 23, 2017

(54) EXTENDED WEAR DEVICES FOR LIQUID DEODORIZERS AND CONTAINERS INCLUDING SUCH DEVICES

(71) Applicant: Cynthia G Timms, Atlanta, GA (US)

(72) Inventor: Cynthia G Timms, Atlanta, GA (US)

(73) Assignee: Emory University, Atlanta, GA (US)

( * ) Notice: Subject to any disclaimer, the term of this patent is extended or adjusted under 35 U.S.C. 154(b) by 533 days.

(21) Appl. No.: 14/348,630

(22) PCT Filed: Nov. 14, 2012

(86) PCT No.: PCT/US2012/064950
§ 371 (c)(1),
(2) Date: Mar. 31, 2014

(87) PCT Pub. No.: WO2013/074582
PCT Pub. Date: May 23, 2013

(65) Prior Publication Data
US 2014/0257215 A1    Sep. 11, 2014

Related U.S. Application Data

(60) Provisional application No. 61/559,885, filed on Nov. 15, 2011.

(51) Int. Cl.
| | | |
|---|---|---|
| *A61F 5/44* | (2006.01) | |
| *A61F 5/441* | (2006.01) | |
| *A61L 2/18* | (2006.01) | |
| *A61L 9/12* | (2006.01) | |

(52) U.S. Cl.
CPC ............... *A61F 5/441* (2013.01); *A61L 2/18* (2013.01); *A61L 9/127* (2013.01)

(58) Field of Classification Search
CPC .................................. A61F 5/441; A61L 2/18
See application file for complete search history.

(56) References Cited

U.S. PATENT DOCUMENTS

| | | | | |
|---|---|---|---|---|
| 2,800,905 A | * | 7/1957 | Simmons | A61M 3/0245 128/DIG. 24 |
| 4,460,367 A | | 7/1984 | Wong et al. | |
| 4,815,590 A | * | 3/1989 | Peppiatt | B65D 81/264 206/204 |

(Continued)

FOREIGN PATENT DOCUMENTS

| | | |
|---|---|---|
| EP | 0970672 A2 | 1/2000 |
| EP | 12850327.3 | 11/2014 |
| GB | 2259858 A | 3/1993 |

OTHER PUBLICATIONS

European Search Report for EP 12 850 327.3, Nov. 26, 2014.

*Primary Examiner* — Susan Su
(74) *Attorney, Agent, or Firm* — Emory Patent Group

(57) ABSTRACT

A device and container, including the device, are configured for deodorizing an effluent, e.g., bodily waste. The device can include a carrier configured to retain a deodorizer fluid and disperse the deodorizer fluid into the effluent; and a mesh film configured to at least partially envelop the carrier. The carrier can include an absorbent material configured to at least one of absorb, retain, and disperse the deodorizer fluid. The device may be removably or fixedly disposed with respect to a container configured to collect the effluent. The device may be preloaded with the deodorizer fluid.

18 Claims, 4 Drawing Sheets

(56) References Cited

U.S. PATENT DOCUMENTS

| | | | | |
|---|---|---|---|---|
| 5,411,496 | A | * | 5/1995 | Homa ................ A61F 5/441 422/5 |
| 5,786,056 | A | * | 7/1998 | Komine ............ A61F 5/445 428/167 |
| 5,860,959 | A | * | 1/1999 | Gent ................ A61L 9/01 604/327 |
| 6,129,716 | A | * | 10/2000 | Steer ................ A61F 5/441 604/332 |
| 6,165,159 | A | * | 12/2000 | Blanton ............ A61F 5/441 604/333 |
| 6,186,990 | B1 | * | 2/2001 | Chen ................ A61F 5/44 4/451 |
| 6,315,767 | B1 | * | 11/2001 | Dumont ............ A61J 1/10 128/DIG. 24 |
| 6,656,169 | B1 | * | 12/2003 | Steer ................ A61F 5/441 604/333 |
| 6,685,684 | B1 | * | 2/2004 | Falconer ............ A61F 5/441 604/332 |
| 6,852,100 | B1 | * | 2/2005 | Gent ................ A61F 5/441 604/333 |
| 2009/0012487 | A1 | * | 1/2009 | Park ................ A61L 15/40 604/359 |
| 2010/0055155 | A1 | | 3/2010 | Timms |
| 2013/0035653 | A1 | * | 2/2013 | Kannankeril ........ A61F 5/445 604/333 |
| 2013/0072885 | A1 | * | 3/2013 | Luther ............ A61F 5/4404 604/333 |
| 2014/0330229 | A1 | * | 11/2014 | Lee ................ A61F 5/441 604/333 |

* cited by examiner

30

30

EXTENDED WEAR DEVICES FOR LIQUID DEODORIZERS AND CONTAINERS INCLUDING SUCH DEVICES

CROSS REFERENCE TO RELATED APPLICATION

This application claims priority to U.S. Provisional Application Ser. No. 61/559,885 filed on Nov. 15, 2011, which is hereby incorporated by this reference in its entirety.

BACKGROUND

Due to heredity, injury, or disease, part or all of the large or small intestine of a person may have to be surgically removed, and the stoma (the remaining end of the large intestine or the small intestine) is brought up to the abdominal surface as an ostomy (a surgically created opening in the body for the discharge of bodily wastes). An ostomy pouch is then placed over the ostomy to collect the bodily wastes. The contents of an ostomy pouch are often a good breeding environment for bacteria, which generate odors. A properly-fitted ostomy pouch generally neither leaks nor smells but the pouch will eventually become full so one must periodically open the tail of the pouch (open end pouch), or detach the pouch from the ostomy (closed end pouch), and then empty the collected bodily wastes from the pouch.

During this emptying process the pouch may not be covering the ostomy, or the tail of the pouch may be open, so any odorous gases in the pouch may escape into the surrounding environment. A deodorizer liquid or tablet is often placed in the ostomy pouch, but the deodorizer only serves to mask, and does not always eliminate, the odors. Furthermore, any deodorizer previously contained in the pouch exits the pouch upon emptying along with the effluent, requiring the reapplication of a deodorizer each time the pouch is emptied.

Thus, there is a need for a deodorizer device configured to eliminate the odors associated with ostomy pouches or other containers configured to collect effluent (e.g., bodily waste).

SUMMARY

The disclosure relates to devices and containers for deodorizing effluent. In some embodiments, the devices may include a carrier configured to retain a deodorizer fluid and disperse the deodorizer fluid into the effluent; and a mesh film configured to at least partially envelop the carrier.

In some embodiments, the carrier may be an absorbent material. The mesh film may be configured to allow two-way flow of the effluent and the deodorizing fluid. In some embodiments, the device may further comprise a space between the carrier and the film, the space being configured to retain the deodorizer fluid.

In some embodiments, the carrier may include a substrate, the substrate configured to at least one of absorb, retain, and disperse the deodorizer fluid. The carrier may include a surface layer, the surface layer being disposed on the substrate and configured for surface wicking. The carrier may have anti-microbial properties.

In some embodiments, the device may include a fastener configured to attach the device to a container configured to collect the effluent. The fastener may be an adhesive.

In some embodiments, the carrier may be preloaded with the deodorizer fluid.

In some embodiments, the disclosure relates to a container configured to collect effluent. The container may include the device for deodorizing an effluent including bodily waste. The device may include a carrier configured to retain a deodorizer fluid and disperse the deodorizer fluid into the effluent; and a mesh film configured to at least partially envelop the carrier. In some embodiments, the device may be fixedly disposed to the container. In other embodiments, the device may be removably disposed to the container.

DESCRIPTION OF THE DRAWINGS

The disclosure can be better understood with the reference to the following drawings and description. The components in the figures are not necessarily to scale, emphasis being placed upon illustrating the principles of the disclosure.

DESCRIPTION OF THE EMBODIMENTS

Figure 1:
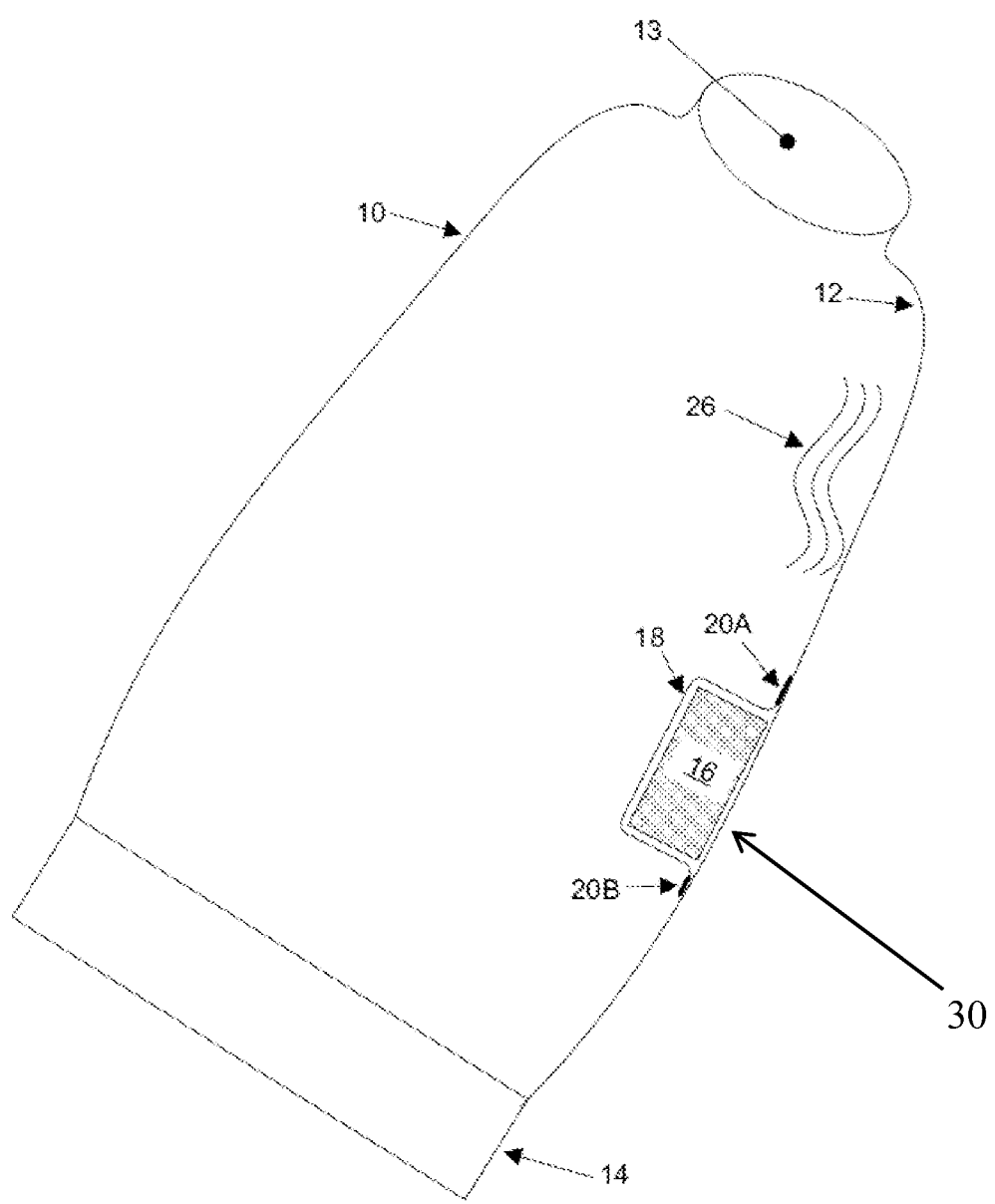
FIG. 1 illustrates an embodiment of an ostomy pouch.

The following description, numerous specific details are set forth such as examples of specific components, devices, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications.

The disclosure relates to deodorizer devices that can be used with containers, for example, an ostomy bag or pouch, configured to collect effluent (e.g., any bodily waste, such as, blood, feces, urine, drainage, etc.) and containers including such deodorizer devices. According to embodiments, the deodorizer devices are configured to neutralize the odors emitted from the container, for example, by retaining and slowly diffusing a deodorizer fluid over the period of wear of the container and thereby may enhance the user's quality of life, particularly in public places. The deodorizer devices are configured so that odor would not escape the pouch each time it is emptied nor require immediate reinsertion of deodorizers into the container to mask odors emitted upon subsequent emptying the pouch. The deodorizer devices and containers according to embodiments thus can eliminate the need for a user to carry deodorizers upon his or her person at all times in an effort to minimize discomfort and embarrassment associated with emitted odors.

FIG. 1 illustrates an embodiment of a container configured to collect effluent. FIG. 1 shows an embodiment of an ostomy pouch (or bag) 10. However, it will be understood that the container may be any container configured to collect effluent, including but not limited to, a fistula pouch, a fecal or urinary bedside drainage bag or any other device or container in which feces or urine can be collected.

The ostomy pouch 10 may be any type of ostomy pouch and is not limited to the construction shown in the FIG. 1. The ostomy pouch 10 may be an open ended pouch, closed ended pouch, a one-piece system, a two-piece system, or some combination thereof.

In some embodiments, the ostomy pouch 10 may include a first surface 12 (also referred to as an "interior" or "inside opening"). In some embodiments, the pouch 10 may include a first opening 13 (also referred to as "entrance opening"), for example, for a closed ended pouch. In the ostomy pouch 10 may further include a second opening 14 (also referred to as a "tail opening"), for example, for an open ended pouch.

In some embodiments, the ostomy pouch 10 may include a deodorizer device 30. The deodorizer device 30 may be configured to neutralize odors associated with the effluent by deodorizing and/or reducing (or suppress) bacterial growth. The deodorizer device 30 may be configured to contact the effluent (e.g., bodily waste) and disperse a deodorizing fluid into the effluent.

In some embodiments, the deodorizer device 30 may include a carrier platform (also referred to as a "carrier") 16. The carrier 16 may include silver ions and/or antimicrobial features. The silver, preferably in the form of a silver compound, and/or the anti-bacterial compounds, may be configured to inhibit or reduce bacterial growth, thereby reducing the odorous gases generated by the bacteria in the effluent.

Figure 2A:
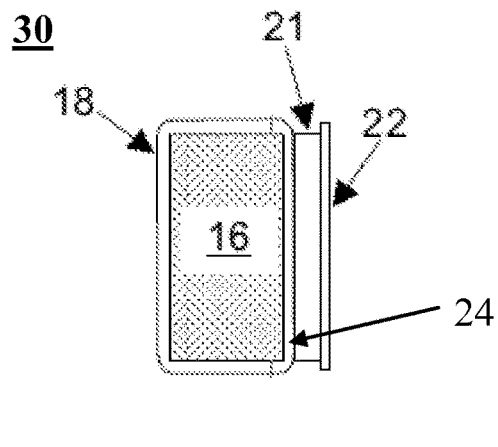
FIGS. 2A-C illustrate embodiments of a deodorizer device.
Figure 2B:
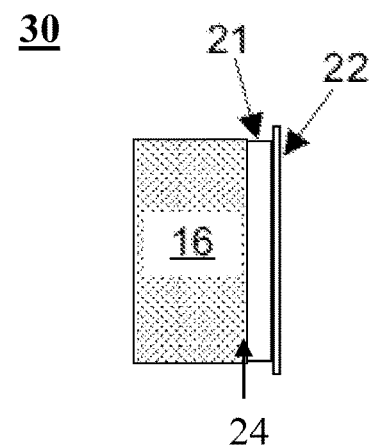
Figure 2C:
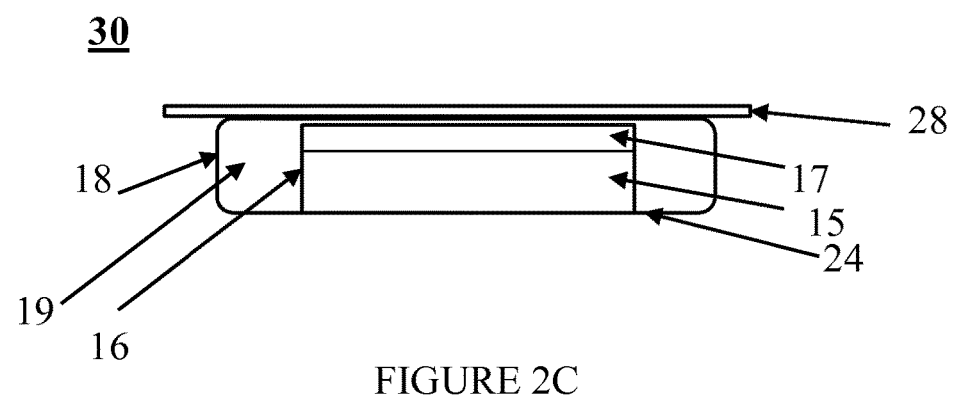

In some embodiments, the carrier 16 may include a base substrate 15, for example, as shown in FIG. 2C. The base substrate 15 may be an absorbent material configured for two-way fluid flow. The base substrate 15 may be configured to retain, as well as disperse, fluid. For example, the base substrate 15 may be filled with a deodorizer fluid, configured to retain a deodorizer fluid and disperse the deodorizer fluid into the effluent when the base substrate 15 absorbs the effluent. In some embodiments, the base substrate 15 may have properties similar to hydrophilic AFM Ultra Ag absorbent pad with silver ions/antimicrobial features, made by Milliken. This product is a medical dressing for a wound. See, for example, U.S. Pat. Nos. 6,584,668 and 6,821,936. Other pads or carriers with silver ions and/or antimicrobial features may also provide the desired bacterial growth suppression.

In some embodiments, the carrier 16 may optionally include a surface layer 17, as shown in FIG. 2C. The surface layer 17 may be a moisture vapor permeable film. The layer 17 may have antimicrobial properties and/or be configured for surface wicking.

In some embodiments, the device 30 may include a mesh or porous film 18 that at least partially envelops or surrounds the carrier 16. The film 18 may include openings configured to allow the deodorizing fluid to move from the carrier 16 into the effluent (not shown). In some embodiments, the device 30 may include a space 19 between the carrier 16 and the mesh film 18. The space 19 may be configured to retain the deodorizer fluid.

In some embodiments, the device 30 may be integrated and/or fixedly (or permanently) fastened to the ostomy pouch 10. In some embodiments, the device 30 may be permanently bonded to an ostomy pouch. In some embodiments, the mesh or vented film 18 may be configured to hold the carrier 16 in place with respect to the ostomy pouch 10. The mesh or vented film 18 may be glued, welded, heat sealed, or bonded by some other convenient technique, to the inside surface 12 of ostomy pouch 10 at several different points, only two of which, 20A, 20B, are shown for clarity of illustration. The mesh or vented film 18 may only need be glued or welded to the ostomy pouch at a sufficient number of points and with sufficient bonding to hold the carrier 16 in the ostomy pouch for the expected duration of use of the pouch. In some embodiments, the device 30 may be configured to be disposed close to the bottom, for example, about 2 inches above the bottom (e.g., second opening 14) of the pouch 10.

In other embodiments, the device 30 may be configured to be attached to an ostomy pouch. The device 30 may further include a fastener 21 to attach the device 30 to an ostomy pouch. The fastener 21 may include but is not limited to an adhesive. In some embodiments, the fastener 21 may be configured to provide sufficient bonding to hold the carrier 16 in the ostomy pouch for the expected duration of use of the pouch. The consumer can then use a new carrier with a clean pouch with each pouch change. In other embodiments, the fastener 21 may be configured to remove the device 30 from a pouch without damaging the pouch so as to allow the device 30 to be replaced in situations, for example, where replacement of the entire ostomy pouch 10 is not convenient. Thus, the device can be readily removed and replaced with a fresh carrier.

In some embodiments, the fastener 21 may be disposed on a surface 24 of the device 30. The surface 24 may be integrated and/or attached to the mesh vented film 18 so that the carrier 16 is completely enveloped or surrounded. The surface 24 may be made of the same material as the film 18 but without the holes. In some embodiments, the fastener 21 may be protected with a protective layer 22. As shown in FIG. 2A, the device 30 may include the carrier 16, enclosed by a mesh or vented film 18 and the surface 24, with fastener 21 disposed on the surface 24, and the protective layer 22 covering the fastener 21. The protective layer 22 can be configured to be removed, such as by peeling it off, to expose the fastener 21. The carrier 16 with the mesh or vented film 18 can then be inserted inside an ostomy pouch, such as the pouch 10, and pressed so that the exposed fastener 21 contacts and sticks to the inner surface 12.

The film 18 may be disposed above one or more surfaces of the carrier 16. In some embodiments, the film 18 may fully surround or envelop the carrier 16. In other embodiments, the film 18 may be at least partially surround or envelope the carrier 16. In some embodiments, the film 18 may be disposed above the top surface (also referred to as "first surface"; e.g., the surface perpendicular to the opening 13), the opposing side surfaces (also referred to as the "second and third surfaces"; e.g., the surfaces parallel to the opening 13), or some combination thereof.

Figure 3A:
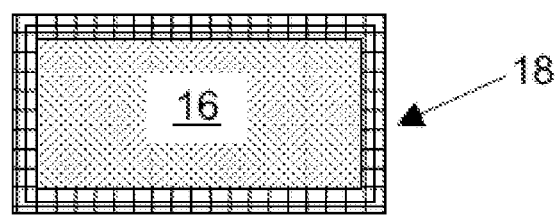
FIGS. 3A and B illustrate embodiments of a deodorizer device.
Figure 3B:
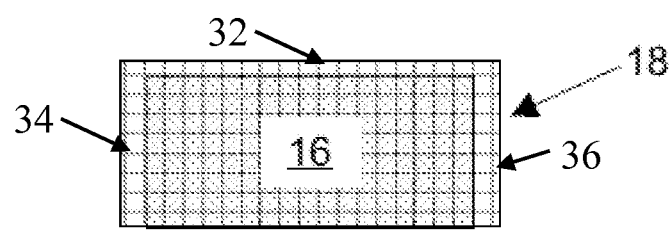

FIGS. 3A and 3B illustrate an end view and a side view, respectively, of the device 30 according to certain embodiments. FIGS. 3A and 3B illustrate the device 30 in which the film 18 partially envelops the carrier 16 by being disposed above surfaces 32, 34, and 36 of the carrier 16. This allows the deodorizing fluid 26 to more easily reach and be absorbed by the carrier 16, rather than having to go through the mesh or film 18 to be absorbed by the carrier 16.

In other embodiments, the device 30 may omit the film 18. FIG. 2B illustrates the device 30 without a mesh or vented film 18 including the fastener 21 covered by the protective layer 22.

In some embodiments, for example, an ostomy pouch may include a pocket for the device 30. The pocket may include at least a section that may be similar to film 18 and may be configured to fixedly hold the device 30, for example, close to the bottom (e.g., about 2 inches above the bottom of the pouch).

Figure 4:
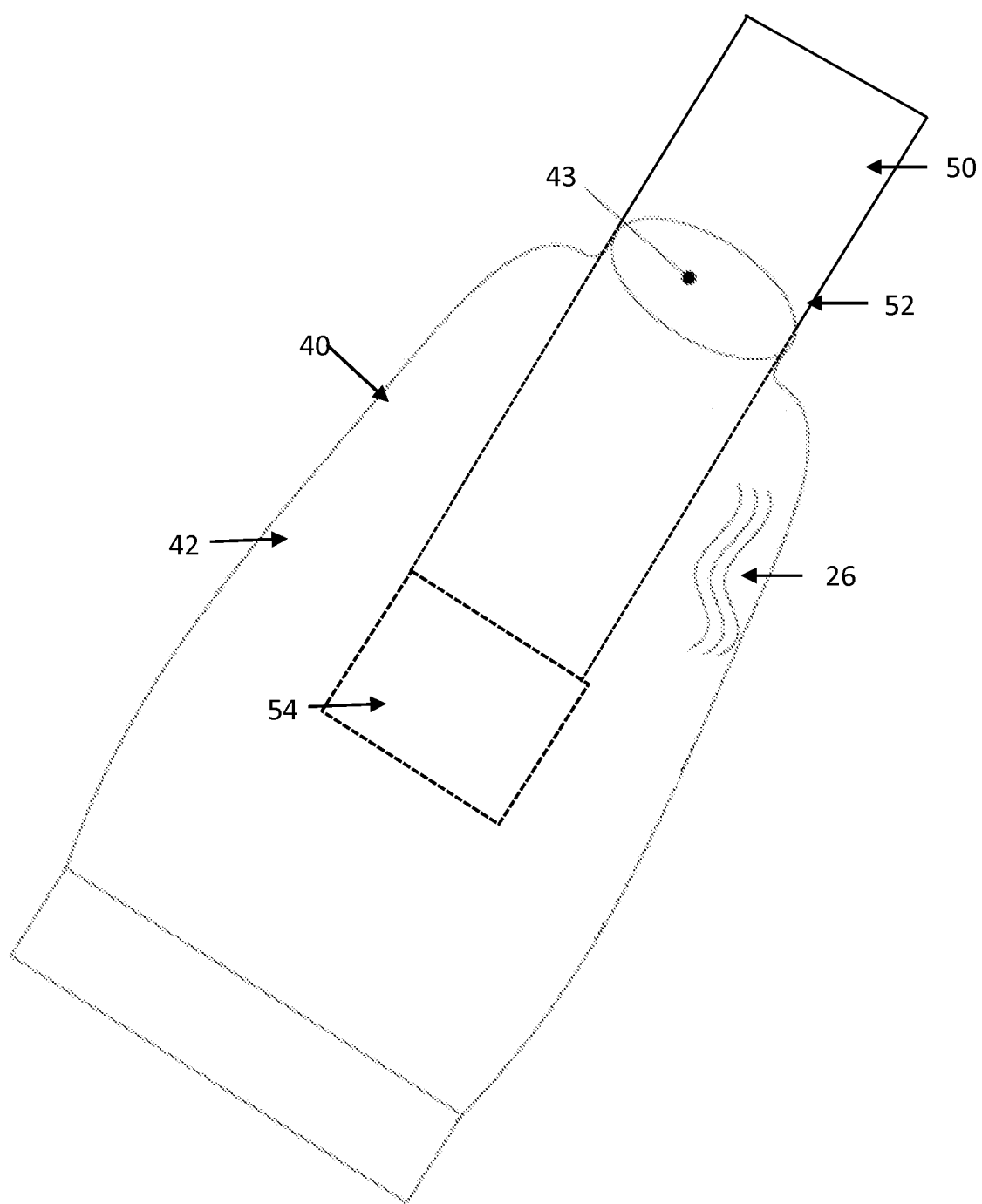
FIG. 4 illustrates embodiments of an ostomy pouch.

FIG. 4 illustrates an example of a container (e.g., ostomy pouch) 40, having a pocket 50 configured to receive a deodorizer device 30. In some embodiments, the ostomy pouch 40 may include a first surface 42 (also referred to as an "interior" or "inside surface") and at least one opening 43. In some embodiments, the pocket 50 may be disposed on one side of the surface 42. In other embodiments, the pocket 50 may be disposed on an outside surface of the pouch 40.

In some embodiments, the pocket 50 may include at least one section. In some embodiments, the pocket 50 includes more than one section, for example, two sections. As shown in FIG. 4, the pocket 50 may include a first section 52 and a second section 54. The first section 52 may be disposed above the second section 54 closer to the opening 43. The second section 54 may be configured to at least temporarily, fixedly hold the device 30. In some embodiments, the second section 54 may at least include a mesh film, like film 18, on one side, configured to allow two-way flow between the effluent and device 30. The film may be disposed to contact the effluent. The first section 52 may be made of a solid (no mesh) material. In some embodiments, the first section 52 may be configured to extend past the opening 43 so that when the pouch 40 is clamped or fastened, the pocket 50 is fixedly closed and sealed.

In some embodiments, the device 30 may be preloaded with a deodorizing fluid 26. The deodorizing fluid 26 can be any commercially available ostomy deodorizing fluid, such as, but not limited to, M9 Drops, Adapt and Ostofresh. The deodorizing fluid may or may not contain silver compounds and/or other antibacterial compounds.

In some embodiments, for example, if the device 30 is preloaded with the deodorizing fluid 26, the device 30 may further include a protective layer 28 configured to cover the film 18 to protect the device 30 and configured to be removed. The protective layer 28 may be for example, a tab, or other mechanism, that may be configured to be removed by pulling, to thereby allow the deodorizing fluid to exit the device 30 into the pouch.

In other embodiments, the deodorizing fluid 26 can be added. In some embodiments, the fluid 26 can be poured or squirted into the pouch 10, or directly onto the carrier 16. The carrier 16 may then absorb the deodorizing fluid 26 and gradually move the deodorizing fluid from the carrier 16 into the effluent. The deodorizing fluid 26 may be introduced via the entrance opening 13 of the pouch and/or the tail opening 14.

Once the deodorizing fluid 26 is absorbed by the carrier 16, the carrier 16 is configured to substantially withhold or retain the fluid 26, although some leakage may occur, until the level of effluent (not shown) in the pouch reaches the level of the carrier. At this point, the carrier 16 is configured to slowly diffuse or disperse the deodorizing fluid through the mesh or vented film 18 into the effluent in the ostomy pouch 10. The carrier 16 thus may also be configured to reduce the amount of deodorizing liquid that is lost when the pouch is emptied.

Thus, the usable wearing time of an ostomy pouch has been extended, thereby providing a convenience and significant cost savings to the user due to less frequent pouch changes as a result of odor. Also, the amount of deodorizing fluid that must be used has been reduced, thereby providing both a convenience and a cost-savings to the user.

Although the preferred embodiment is for the carrier to have the silver ions and/or antimicrobial features, the carrier may also be an untreated carrier, in which case the silver ions and/or antimicrobial compounds would be applied to the carrier, such as in the form of a liquid. In this case, if desired, the silver ions and/or antimicrobial compounds may be included in the deodorizing liquid 26.

It will be understood that although the deodorizing device 30 has been primarily described for use with an ostomy pouch, the device 30 can also be used with a fistula pouch, a fecal or urinary bedside drainage pouch or any other device or container in which feces or urine is collected.

According to some embodiments, the deodorizing device 30 may be single use or be disposable. According to some embodiments, a portion or any combination of the devices, containers or pouches, and/or deodorizing fluids may be sold as a kit.

In some embodiments, the kit may include at least one deodorizing device, according to embodiments, and deodorizing fluid. In some embodiments, the kit may include a plurality of deodorizing devices and a bottle of deodorizing fluid.

In other embodiments, the kit may include a plurality of deodorizing devices preloaded with a deodorizing fluid. In further embodiments, the kit may also include a bottle of a deodorizing fluid.

In some embodiments, the kit may include at least one ostomy pouch or other kind of drainage pouches, containers or devices. In some embodiments, the pouch may include the deodorizing device. In other embodiments, the kit may include at least one deodorizing devices. In further embodiments, the kit may include a plurality of pouches and devices, optionally preloaded with a deodorizing fluid. The kit may also include a bottle of deodorizing fluid.

In some embodiments, the kit may include a port configured to infuse the deodorizer fluid into the effluent.

While various embodiments of the disclosure have been described, the description is intended to be exemplary rather than limiting and it will be apparent to those of ordinary skill in the art that may more embodiments and implementations are possible that are within the scope of the disclosure.

What is claimed:

1. A device for deodorizing effluent, comprising:
   a carrier configured to retain a deodorizer fluid and disperse the deodorizer fluid into the effluent; and
   a mesh film configured to at least partially envelop the carrier,
   wherein the carrier includes a substrate, the substrate configured to at least one of absorb, retain, and disperse the deodorizer fluid, and
   wherein the carrier includes a surface layer, the surface layer being disposed on the substrate and configured for surface wicking.

2. The device according to claim 1, wherein the carrier is an absorbent material.

3. The device according to claim 1, wherein the mesh film is configured to allow two-way flow of the effluent and the deodorizing fluid.

4. The device according to claim 1, further comprising a space between the carrier and the mesh film, the space being configured to retain the deodorizer fluid.

5. The device according to claim 1, wherein the carrier has anti-microbial properties.

6. The device according to claim 1, further comprising:
   a fastener configured to attach the device to a container configured to collect the effluent.

7. The device according to claim 6, wherein the container is a pouch or a bag.

8. The device according to claim 1, wherein the carrier is preloaded with the deodorizer fluid.

9. A container configured to collect effluent, the container comprising:

a device for deodorizing the effluent, the device including:
- a carrier configured to retain a deodorizer fluid and disperse the deodorizer fluid into the effluent; and
- a mesh film configured to at least partially envelop the carrier,
- wherein the carrier includes a substrate, the substrate configured to at least one of absorb, retain, and disperse the deodorizer fluid, and
- wherein the carrier includes a surface layer, the surface layer being disposed on the substrate and configured for surface wicking.

10. The container according to claim 9, wherein the carrier is an absorbent material.

11. The container according to claim 9, wherein the mesh film is configured to allow two-way flow of the effluent and the deodorizing fluid.

12. The container according to claim 9, wherein the device includes a space between the carrier and the mesh film, the space being configured to retain the deodorizer fluid.

13. The container according to claim 9, wherein the carrier has anti-microbial properties.

14. The container according to claim 9, further comprising:
- a fastener configured to attach the device to the container.

15. The device according to claim 14, wherein the container is a pouch or a bag.

16. The container according to claim 9, wherein the carrier is preloaded with the deodorizer fluid.

17. The container according to claim 9, wherein the device is fixedly disposed to the container.

18. The container according to claim 9, wherein the device is removably disposed to the container.

* * * * *